United States Patent [19]

Shirafuji et al.

[11] Patent Number: 5,218,129

[45] Date of Patent: Jun. 8, 1993

[54] PROCESS FOR PRODUCING 3,4-DIHYDROCOUMARIN

[75] Inventors: Tamio Shirafuji; Kiyomi Sakai; Kensen Okusako; Yoshitaka Nishida, all of Ehime, Japan

[73] Assignee: Sumitomo Chemical Co., Ltd., Osaka, Japan

[21] Appl. No.: 808,499

[22] Filed: Dec. 17, 1991

[30] Foreign Application Priority Data

Dec. 19, 1990 [JP] Japan ................................ 2-403517
Aug. 30, 1991 [JP] Japan ................................ 3-219768

[51] Int. Cl.$^5$ .......................................... C07D 311/20
[52] U.S. Cl. ................................................... 549/290
[58] Field of Search ........................................ 549/290

[56] References Cited

U.S. PATENT DOCUMENTS 3,442,910 5/1989 Thweatt ........................... 549/290

FOREIGN PATENT DOCUMENTS 0434410 6/1991 European Pat. Off. .
2502690 7/1975 Fed. Rep. of Germany ...... 549/290
1443406 7/1976 United Kingdom .

OTHER PUBLICATIONS

Chemical Abstracts, vol. 115, No. 17, Oct. 28, 1991, p. 905, 183103w and 183104x.

Primary Examiner—C. Warren Ivy
Assistant Examiner—Ba K. Trinh
Attorney, Agent, or Firm—Sughrue, Mion, Zinn, Macpeak & Seas

[57] ABSTRACT

A process for producing 3,4-dihydrocoumarin comprising cyclization and dehydrogenation of a 3-(2-cyclohexanoyl)propionic acid ester, in which a reaction mixture obtained by the cyclization and dehydrogenation is washed with an alkali to reduce the dihydrocinnamic acid content of the reaction mixture to 1% by weight or less and/or previously distilling the reaction mixture to remove high-boiling substances, and then subjected to rectification to recover 3,4-dihydrocoumarin. The thus obtained 3,4-dihydrocoumarin has high purity and high quality sufficient for use as a perfume as it is.

7 Claims, No Drawings

PROCESS FOR PRODUCING 3,4-DIHYDROCOUMARIN

FIELD OF THE INVENTION

The present invention relates to a process for producing 3,4-dihydrocoumarin from 3-(2-cyclohexanoyl)propionic acid esters. 3,4-Dihydrocoumarin is an important compound in the perfume industry and is also useful as an intermediate for dyes, agricultural chemicals or pharmaceuticals.

BACKGROUND OF THE INVENTION 3,4-Dihydrocoumarin is obtained by cyclization and dehydrogenation of a 3-(2-cyclohexanoyl)propionic acid ester in the presence of a solid metallic catalyst, etc. Coumarin by-produced by the reaction is separated from the reaction mixture by distillation, crystallization or the like means for use as a product. The by-produced coumarin may also be converted to 3,4-dihydrocoumarin by partial hydrogenation.

Other by-products resulting from the above reaction mainly include compounds having a lower boiling point than 3,4-dihydrocoumarin, e.g., ethylbenzene, o-ethylphenol, and a dihydrocinnamic acid ester; compounds having a higher boiling point than 3,4-dihydrocoumarin, such as esters (e.g., o-ethylphenyl 3-cyclohexylpropionate and o-ethylphenyl dihydrocinnamate), octahydrocoumarin, and dihydrocinnamic acid; and tar-like substances. In order to remove these by-products, the reaction mixture per se has conventionally been subjected to rectification to recover 3,4-dihydrocoumarin.

However, the conventional purification process being followed, o-ethylphenol and dihydrocinnamic acid are incorporated into the 3,4-dihydrocoumarin fraction during rectification to reduce the purity of the resulting 3,4-dihydrocoumarin.

Because o-ethylphenol has a low boiling point and gives off a phenol-like smell, it deteriorates the odor of 3,4-dihydrocoumarin for use as a perfume. Therefore, there is a demand to reduce the o-ethylphenol content in the resulting 3,4-dihydrocoumarin to about 0.05% by weight or less.

Similarly, dihydrocinnamic acid has a cinnamon-like smell and deteriorates the odor of 3,4-dihydrocoumarin for use as a perfume. Therefore, there is a demand to reduce the dihydrocinnamic acid content in 3,4-dihydrocoumarin to about 0.05% by weight or less.

In order to recover high purity 3,4-dihydrocoumarin free from impurities, complicated steps such as repetition of rectification have been required, and it also leads to a loss of 3,4-dihydrocoumarin.

SUMMARY OF THE INVENTION

An object of the present invention is to provide a process for producing 3,4-dihydrocoumarin having sufficient purity and quality for use as a perfume.

Other objects and effects of the present invention will be apparent from the following description.

In the course of studies, the present inventors have found that o-ethylphenol esters, e.g., o-ethylphenyl 3-cyclohexylpropionate and o-ethylphenyl dihydrocinnamate, thermally decompose into o-ethylphenol and carboxylic acids, e.g., 3-cyclohexylpropionic acid and dihydrocinnamic acid, during rectification of the reaction mixture and that the thus released o-ethylphenol is distilled off together with 3,4-dihydrocoumarin. As a result of further extensive investigations, the inventors have also found that 3,4-dihydrocoumarin of high purity and high quality sufficient for use as a perfume can easily be recovered from the reaction mixture by previously distilling the reaction mixture to once separate high-boiling substances and/or washing the reaction mixture or the distillate with an alkali to remove acidic compounds such as dihydrocinnamic acid, followed by rectification. The present invention has been completed based on these findings.

The present invention relates to a process for producing 3,4-dihydrocoumarin comprising cyclization and dehydrogenation of a 3-(2-cyclohexanoyl)propionic acid ester, in which the reaction mixture of the cyclization and dehydrogenation is washed with an alkali to reduce the dihydrocinnamic acid content of the reaction mixture to 1% by weight or less and/or previously distilling the reaction mixture to remove high-boiling substances, and then subjected to rectification to recover 3,4-dihydrocoumarin.

DETAILED DESCRIPTION OF THE INVENTION

Specific but non-limiting examples of the starting compound, i.e., 3-(2-cyclohexanoyl)propionic acid ester, include methyl 3-(2-cyclohexanoyl)propionate, ethyl 3-(2-cyclohexanoyl)propionate, propyl 3-(2-cyclohexanoyl)propionate, butyl 3-(2-cyclohexanoyl)propionate, and isopropyl 3-(2-cyclohexanoyl)propionate.

Cyclization and dehydrogenation reaction of the 3-(2-cyclohexanoyl)propionic acid ester is carried out by heating in the presence of a catalyst. Catalysts to be used are solid metallic catalysts comprising a metal, e.g., palladium, platinum, rhodium, and ruthenium, supported on at least one carrier selected from the group consisting of an element of Group IIA, IIIA or IVA and a compound thereof, e.g., carbon, alumina, silica gel, and barium sulfate. A palladium-on-carrier catalyst is preferred.

The catalyst is generally used in an amount of about from 0.1 to 5% by weight, and preferably of from 0.3 to 2% by weight, based on the 3-(2-cyclohexanoyl)propionic acid ester, although depending on its metal content. Too small an amount of the catalyst results in considerably reduced reaction activity, and too large an amount gives rise to excessive reaction activity resulting in many by-products and an increase in the catalyst cost.

If desired, the solid metallic catalyst may be used in combination which a promotor, such as metallic chromium, metallic tungsten, barium sulfate, magnesium trisilicate, and zirconia. The promotor is generally used in an amount of about from 0.01 to 3% by weight based on the 3-(2-cyclohexanoyl) propionic acid ester.

The cyclization and dehydrogenation reaction is generally effected at about from 100° to 350° C., and preferably from 230° to 300° C. At temperatures lower than about 100° C., the reaction rate tends to be low. At temperatures exceeding 350° C., the starting material and/or the product tend to decompose.

A reaction solvent may be used if desired. Examples of suitable solvents include phenyl ether, benzyl ether, methy- α-naphthyl ether, ethylnaphthalene, dimethylbiphenyl, dodecane, tetradecane, tetralin, acetophenone, phenyl propyl ketone, methyl benzoate, and dimethyl glutamate.

The reaction is generally carried out by heating the 3-(2-cyclohexanoyl)propionic acid ester and the catalyst along with, if desired, a promotor and a solvent for several hours to several tens of hours.

The reaction generally affords 3,4-dihydrocoumarin in a yield of about from 30 to 70 mol% and coumarin in a yield of about from 5 to 35 mol%. The reaction by-produces dihydrocinnamic acid in a yield of about from 0.1 to 20% by weight based on 3,4-dihydrocoumarin and o-ethylphenyl 3-cyclohexyl-propionate and o-ethylphenyl dihydrocinnamate in a total yield of about from 2 to 20% by weight based on 3,4-dihydrocoumarin. Besides these by-products, ethylbenzene, o-ethylphenol, a dihydrocinnamic ester, octahydrocoumarin, and tar-like substances are also by-produced.

The resulting reaction mixture of cyclization and dehydrogenation may be subjected to hydrogenation to convert coumarin present therein to 3,4-dihydrocoumarin.

In the present invention, the reaction mixture obtained by the cyclization and dehydrogenation reaction is then subjected to alkali washing for removal of acidic compounds and/or distillation for removal of high-boiling substances. Alkali washing is performed either before or after distillation.

Alkalis which can be used for removal of acidic compounds include hydroxides, oxides, carbonates, hydrogencarbonates, hydrogenphosphates, and dihydrogenphosphates of alkali metals or alkaline earth metals, and compounds showing basicity when dissolved in water. Specific examples of the alkali include lithium hydroxide, sodium hydroxide, potassium hydroxide, magnesium hydroxide, calcium hydroxide, magnesium oxide, calcium oxide, sodium carbonate, potassium carbonate, magnesium carbonate, calcium carbonate, barium carbonate, sodium hydrogencarbonate, potassium hydrogencarbonate, disodium hydrogenphosphate, dipotassium hydrogenphosphate, sodium dihydrogenphosphate, and potassium dihydrogenphosphate.

Alkali washing is carried out by bringing the reaction mixture (or a distillate in case where distillation precedes alkali washing, hereinafter the same) with an alkali. For example, the contact may be effected by mixing with stirring, counter-flow or direct-flow contact, passing the reaction mixture through a pack of an alkali, or passing an alkali through a pack of the reaction mixture.

While the alkali may be used as a solid, it is preferably used as an aqueous solution for ease of handling. In the latter case, the aqueous solution preferably has a concentration of about from 0.1 to 50% by weight, and more preferably about from 1 to 10% by weight and less than the saturation point. If the concentration is less than about 0.1% by weight, sufficient washing effects cannot be obtained. If it exceeds about 50% by weight, hydrolysis of 3,4-dihydrocoumarin tends to be accelerated. Concentrations above the saturation point are employable but make the operation complicated.

The amount of the alkali to be used, though varying depending on the manner of contact or the concentration of dihydrocinnamic acid, generally ranges about from 0.1 to 100 equivalents per equivalent of dihydrocinnamic acid. If it is less than about 0.1 equivalent, sufficient washing effects cannot be obtained. If it exceeds about 100 equivalents, hydrolysis of 3,4-dihydrocoumarin tends to be accelerated.

Where an alkali metal or alkaline earth metal hydroxide is used as an alkali or where an aqueous solution of an alkali metal or alkaline earth metal oxide is used as a substantial hydroxide, it is preferably used in an amount of not more than about 1.5 equivalents per equivalent of dihydrocinnamic acid. If such a strong alkali is used in an amount of more than 1.5 equivalents, hydrolysis of 3,4-dihydrocoumarin tends to be unfavorably accelerated.

Where an alkali aqueous solution is employed, it is preferably used in an amount of about from 0.1 to 10 times the weight of the reaction mixture. If it is smaller than 0.1 times, sufficient washing effects cannot be obtained. If it is larger than 10 times, it tends to result in not only an increased loss of 3,4-dihydrocoumarin into the alkaline aqueous solution but accelerated hydrolysis of 3,4-dihydrocoumarin.

It is preferable to conduct alkali washing so as to reduce the dihydrocinnamic acid content to about 1% by weight or less based on 3,4-dihydrocoumarin. With respect to a mixture containing 3,4-dihydrocoumarin having a dihydrocinnamic acid content of about 1% by weight or less based on 3,4-dihydrocoumarin, the subsequent rectification would provide high purity 3,4-dihydrocoumarin having sufficient quality suitable for use as a perfume as it is. If the dihydrocinnamic acid content is more than 1% by weight based on 3,4-dihydrocoumarin, the subsequent rectification tends to result in recovery of poor quality 3,4-dihydrocoumarin having a high dihydrocinnamic acid content which is unsuitable for use as a perfume as it is.

After the alkali washing, the mixture may further be washed with water to remove the remaining alkali.

Simple distillation suffices for removal of high-boiling substances. Distillation may be effected while refluxing at a reflux ratio of not more than 5. Distillation may also be effected in a packed tower or a plate tower having a number of stages of 10 or less. Distillation at a reflux ratio of 5 or more or 10 or more-staged distillation is substantially equal to rectification which is complicated.

Distillation is generally carried out under a pressure of about from 0.1 to 100 Torr. Distillation under a pressure lower than about 0.1 Torr not only requires large-scaled equipment for pressure reduction but has a decreased rate of distillation, leading to reduction in productivity. If the pressure is higher than about 100 Torr, the temperature of the still pot must be so increased, and the increased temperature of the distillation pot tends to cause decomposition of 3,4-dihydrocoumarin.

Distillation for removal of high-boiling substances is preferably conducted so as to reduce the total content of o-ethylphenyl 3-cyclohexylpropionate and o-ethylphenyl dihydrocinnamate to about 2% by weight or less, and particularly 1% by weight or less, based on the amount of 3,4-dihydrocoumarin.

Although compounds forming o-ethylphenol during rectification are not limited to o-ethylphenyl 3-cyclohexylpropionate and o-ethylphenyl dihydrocinnamate, production of o-ethylphenol during rectification can sufficiently be minimized to recover 3,4-dihydrocoumarin having high purity and sufficient quality for use as a perfume by controlling the total content of these ester compounds to 2% weight or less based on 3,4-didydrocoumarin.

Rectification for obtaining high purity 3,4-dihydrocoumarin can be conducted by use of a packed tower or a plate tower. A suitable number of stages of the tower is about from 5 to 100. If the number of stages is less than about 5, separation efficiency tends to be reduced, failing to obtain 3,4-dihydrocoumarin of sufficiently high purity. If the number of stages is more than about 100, large-scaled equipment is required. A reflux ratio, while dependent on the number of stages, preferably ranges about from 1 to 50, and more preferably about from 5 to 20. If the reflux ratio is less than about 1, separation efficiency tends to be deteriorated, failing to obtain 3,4-dihydrocoumarin having sufficient purity. If it is more than about 50, the energy for refluxing is much increased.

The rectification is generally carried out under a pressure of about from 0.1 to 100 Torr. Rectification under a pressure of less than about 0.1 Torr not only requires a large-scaled apparatus for pressure reduction but also has a reduced rate of distillation, resulting in deterioration of efficiency. If the pressure is higher than about 100 Torr, the temperature of the still pot must be elevated accordingly, and the elevated distillation temperature tends to cause decomposition of 3,4-dihydrocoumarin, o-ethylphenyl 3-cyclohexylpropionate, o-ethylphenyl dihydrocinnamate, etc.

By the process of the present invention, 3,4-dihydrocoumarin having high purity and high quality sufficient for use as a perfume as such can easily be obtained from 3-(2-cyclohexanoyl)propionic acid esters.

The present invention is now illustrated in greater detail by reference to the following Examples, but it should be understood that the present invention is not construed to be limited thereto. All the percents are by weight unless otherwise indicated.

EXAMPLE 1

In a 1 l- volume four-necked flask were charged 308 g of methyl 3-(2-cyclohexanoyl)propionate and 3.0 g of a 5% palladium-on-carbon catalyst (5% of palladium was supported on an activated carbon carrier). The mixture was heated at 240° C. for 10 hours while stirring at 300 rpm in a nitrogen atmosphere to conduct cyclization and dehydrogenation. Thereafter, the mixture was further heated while stirring at 300 rpm at 255° C. for 1 hour and then at 270° C. for 16 hours. After completion of the cyclization and dehydrogenation reaction, the catalyst and the like were removed by filtration to obtain 207 g of a reaction mixture.

Cyclization and dehydrogenation reaction of methyl 3-(2-cyclohexanoyl)propionate was conducted two more times in the same manner as described above. The three reaction mixtures combined weighing 624 g were found to comprise 48.1% of 3,4-dihydrocoumarin, 33.7% of coumarin, 5.3% of the sum of o-ethylphenyl 3-cyclohexylpropionate and o-ethylphenyl dihydrocinnamate, and 0.6% of dihydrocinnamic acid. Accordingly, the total content of o-ethylphenyl 3-cyclohexylpropionate and o-ethylphenyl dihydrocinnamate was 11.0%, and the content of dihydrocinnamic acid was 1.2%, both based on the amount of 3,4-dihydrocoumarin.

In a 1 separatory funnel were charged 585 g of the above-obtained combined reaction mixture and 586 g of a 5% sodium hydrogencarbonate aqueous solution, the amount of sodium hydrogencarbonate corresponding to 14.9 equivalents per equivalent of dihydrocinnamic acid. The mixture was stirred at 400 rpm at room temperature for 20 minutes, followed by allowing to stand at room temperature for 1 hour to separate into an upper aqueous phase and a lower oily phase. The resulting oily phase and 583 g of water were charged in a 1 separatory funnel, and the mixture was stirred at room temperature and at 400 rpm for 20 minutes, followed by allowing to stand at room temperature for 1 hour whereby the mixture was separated into an upper aqueous phase and a lower oily phase. The separated oily phase weighed 572 g. As a result of gas chromatography of the washed oily phase, the dihydrocinnamic acid concentration was below the limit of detection and was thus found to be not more than 1% based on 3,4-dihydrocoumarin. The yield of 3,4-dihydrocoumarin in the above-described alkali washing was 99.0%. A 565 g aliquot of the resulting washed oily phase was subjected to simple distillation at 10 Torr to remove high-boiling substances to recover 460 g of crude 3,4-dihydrocoumarin. The resulting crude product was found to contain 54.8% of 3,4-dihydrocoumarin, 32.7% of coumarin, and 0.16% of the sum of o-ethylphenyl 3-cyclohexylpropionate and o-ethylphenyl dihydrocinnamate, with the concentration of dihydrocinnamic acid being below the limit of detection. Accordingly, the total content of o-ethylphenyl 3-cyclohexylpropionate and o-ethylphenyl dihydrocinnamate was 0.29%, and the content of dihydrocinnamic acid was not more than 1%, both based on the amount of 3,4-dihydrocoumarin.

The above crude product was subjected to rectification by using a 33-staged packed tower at a reflux ratio of 10 under a pressure of 20 Torr. As a result, 172 g of purified 3,4-dihydrocoumarin was obtained in a yield of 61% based on the 3,4-dihydrocoumarin present in the cyclization and dehydrogenation reaction mixture. The thus purified product had a 3,4-dihydrocoumarin purity of 99.7% and an o-ethylphenol content of 0.05%, with the dihydrocinnamic acid content being below the limit of detection of gas chromatography.

COMPARATIVE EXAMPLE 1

In a 1 l four-necked flask were charged 411 g of methyl 3-(2-cyclohexanoyl)propionate and 8.0 g of a 5% palladium-on-carbon catalyst. The mixture was heated at 240° C. for 8.5 hours while stirring at 300 rpm in a nitrogen atmosphere to conduct cyclization and dehydrogenation. Thereafter, the reaction mixture was further heated at 250° C for 5.5 hours and then at 260° C. for 16 hours with stirring at 300 rpm. After completion of the cyclization and dehydrogenation reaction, the catalyst and the like were removed by filtration to obtain 232 g of a reaction mixture.

The same reaction was repeated to obtain 557 g of a reaction mixture in total. The resulting combined reaction mixture had a 3,4-dihydrocoumarin content of 42.3%, a coumarin content of 39.9%, a total content of o-ethylphenyl 3-cyclohexylpropionate and o-ethylphenyl dihydrocinnamate of 6.6%, and a dihydrocinnamic acid content of 1.1%. Accordingly, the total content of o-ethylphenyl 3-cyclohexylpropionate and o-ethylphenyl dihydrocinnamate was 15.6%, and the content of dihydrocinnamic acid was 2.6%, both based on the amount of 3,4-dihydrocoumarin.

A 342 g aliquot of the resulting reaction mixture was rectified in a 33-staged packed tower at a reflux ratio of 10 under a pressure of 20 Torr to recover 93.5 g of purified 3,4-dihydrocoumarin in a yield of 65% based on the 3,4-dihydrocoumarin present in the reaction mixture. The purity of 3,4-dihydrocoumarin in the purified product was 98.2%; the o-ethylphenol content was 1.0%; and the dihydrocinnamic acid content was 0.06%. The product as obtained was unsuitable for use as a perfume.

EXAMPLE 2

In a 1 l-volume four-necked flask were charged 606 g of methyl 3-(2-cyclohexanoyl)propionate and 6.1 g of a 5% palladium-on-carbon catalyst. The mixture was heated at 250° C. for 15.5 hours while stirring at 300 rpm in a nitrogen atmosphere to conduct cyclization and dehydrogenation. Thereafter, the mixture was further heated at 260° C. with stirring at 300 rpm for 3 hours.

The resulting reaction mixture as containing the catalyst was transferred to a 1 l glass-made autoclave in air and heated at 120° C. for 70 minutes at a hydrogen pressure of 2 kg cm$^2$ while stirring at 1,000 rpm to conduct hydrogenation. After completion of the hydrogenation reaction, the catalyst and the like were removed from the reaction mixture by filtration to obtain 389 g of a hydrogenation reaction mixture. The resulting reaction mixture had a 3,4-dihydrocoumarin content of 67.4%, a total content of o-ethylphenyl 3-cyclohexylpropionate and o-ethylphenyl dihydrocinnamate of 11.4%, and a dihydrocinnamic acid content of 1.15%. Accordingly, the total content of o-ethylphenyl 3-cyclohexylpropionate and o-ethylphenyl dihydrocinnamate was 16.9%, and the dihydrocinnamic acid content was 1.71%, both based on the amount of 3,4-dihydrocoumarin.

The resulting reaction mixture was subjected to simple distillation at 10 Torr to remove high-boiling substances to thereby recover 344 g of crude 3,4-dihydrocoumarin as a distillate.

A 339 g aliquot of the distillate was washed successively with 339 g of a 5% sodium hydrogencarbonate aqueous solution and 165 g of water to obtain 322 g of crude 3,4-dihydrocoumarin, in which the 3,4-dihydrocoumarin content was 80.5%; the total content of o-ethylphenyl 3-cyclohexylpropionate and o-ethylphenyl dihydrocinnamate was 0.79%, and the dihydro-cinnamic acid content was 0.38%. Accordingly, the total content of o-ethylphenyl 3-cyclohexylpropionate and o-ethylphenyl dihydrocinnamate was 0.98%, and the dihydrocinnamic acid content was 0.47%, both based on 3,4-dihydrocoumarin.

A 202 g aliquot of the resulting crude 3,4-dihydrocoumarin was subjected to rectification in a 33-staged packed tower at a reflux ratio of 10 at a pressure of 5 Torr to recover 126 g of purified 3,4-dihydrocoumarin in a yield of 77% based on the 3,4-dihydrocoumarin charged in the packed tower. The purity of 3,4-dihydrocoumarin was 99.7%; the o-ethylphenol content was 0.032%; and the dihydrocinnamic acid content was below the limit of detection of gas chromatography.

EXAMPLE 3

In a 500 ml separatory funnel were charged 150 g of 3,4-dihydrocoumarin containing 4.0% of dihydrocinnamic acid and 150 g of a 5% sodium hydrogencarbonate aqueous solution. The amount of sodium hydrogencarbonate corresponded to 2.2 equivalents per equivalent of dihydrocinnamic acid. The mixture was stirred at room temperature at 400 rpm for 20 minutes, followed by allowing to stand at room temperature for 1 hour to separate into an upper aqueous phase and a lower oily phase. In a 500 ml separatory funnel were charged the thus separated oily phase and 150 g of water and stirred at 400 rpm at room temperature for 20 minutes, followed by allowing to stand at room temperature for 1 hour to separate into an upper aqueous phase and a lower oily phase to obtain 144 g of a washed oily phase. As a result of gas chromatography, the washed oily phase was found to have a dihydrocinnamic acid content of 0.16%, which corresponded to not more than 1% based on 3,4-dihydrocoumarin. The yield of 3,4-dihydrocoumarin in the above alkali washing was 99.1%.

EXAMPLE 4

3,4-Dihydrocoumarin having a varied content of dihydrocinnamic acid was washed with an alkali in the same manner as in Example 3, except for changing the kind and amount of the alkali used as shown in Table 1 below. The results obtained are shown in Table 1.

TABLE 1

| | Sample. No. | | | | | | | |
|---|---|---|---|---|---|---|---|---|
| | 1 | 2 | 3 | 4 | 5 | 6 | 7 | 8 |
| HCA Concentration in Oily Phase (wt %) | 4.0 | 7.0 | 7.0 | 7.0 | 7.0 | 4.0 | 7.0 | 1.0 |
| Alkali: | | | | | | | | |
| Kind | NaHCO$_3$ | NaHCO$_3$ | NaHCO$_3$ | NaHCO$_3$ | NaOH | Na$_2$CO$_3$ | Na$_2$CO$_3$ | Na$_2$CO$_3$ |
| Concentration (wt %) | 5 | 5 | 5 | 5 | 2 | 6 | 6 | 6 |
| Aqueous Phase/Oily Phase Weight Ratio | 1.2 | 1.0 | 1.2 | 1.4 | 1.0 | 1.0 | 1.0 | 1.0 |
| Alkali/HCA Equivalent Ratio | 1.9 | 1.3 | 1.5 | 1.8 | 1.1 | 4.2 | 2.4 | 17.0 |
| Washed Oily Phase: | | | | | | | | |
| HCA Concentration (wt %) | 0.12 | 0.94 | 0.68 | 0.47 | 0.39 | N.D. | N.D. | N.D. |
| DHCM Concentration (wt %) | 99.2 | 97.1 | 96.9 | 98.3 | 97.7 | 97.9 | 96.9 | 99.2 |
| HCA/DHCM (wt %) | 0.12 | 0.97 | 0.70 | 0.48 | 0.40 | ≦0.01 | ≦0.01 | ≦0.01 |
| DHCM Yield (%) | 99.9 | 98.0 | 96.9 | 97.3 | 97.1 | 97.1 | 97.8 | 96.5 |

Note:
HCA: Dihydrocinnamic acid
DHCM: 3,4-Dihydrocoumarin
N.D.: Below limit of detection

COMPARATIVE EXAMPLE 2

Alkali washing of dihydrocinnamic acid-containing 3,4-dihydrocoumarin was carried out in the same manner as in Example 3, except for using 2% sodium hydroxide aqueous solution, the amount of sodium hydroxide corresponding to 1.9 equivalents per equivalent of dihydrocinnamic acid. As a result, the dihydrocinnamic acid content in the washed oily phase was below the limit of detection, i.e., not more than 1% based on 3,4-dihydrocoumarin, but the yield of 3,4-dihydrocoumarin was 92.1%.

EXAMPLE 5

In a 500 ml separatory funnel were charged 165 g of 3,4-dihydrocoumarin containing 7.0% of dihydrocinnamic acid and 165 g of a 10% aqueous solution of disodium hydrogenphosphate dodecahydrate. To the mixture was added 15.1 g of a 20% sodium hydroxide aqueous solution while stirring at room temperature. The amount of sodium hydroxide added corresponded to 0.98 equivalent per equivalent of dihydrocinnamic acid, and the total amount of disodium hydrogen phosphate and sodium hydroxide corresponded to 2.2 equivalents per equivalent of dihydrocinnamic acid. The mixture was further stirred at 400 rpm at room temperature for 20 minutes, followed by allowing to stand at room temperature for 1 hour to separate into an upper aqueous phase and a lower oily phase to obtain 151 g of a washed oily phase. As a result of gas chromatography, the washed oily phase was found to have a dihydrocinnamic acid content of 0.05%, which corresponded to not more than 1% based on 3,4-dihydrocoumarin. The yield of 3,4-dihydrocoumarin in the above alkali washing was 97.4%.

EXAMPLE 6

In a 500 ml separatory funnel were charged 165 g of 3,4-dihydrocoumarin containing 7.0% of dihydrocinnamic acid and 165 g of a 1.8% sodium hydrogencarbonate aqueous solution. The mixture was stirred at room temperature at 400 rpm for 20 minutes, followed by allowing to stand at room temperature for 1 hour to separate into an upper aqueous phase and a lower oily phase. As a result of gas chromatography, the washed oily phase was found to have a dihydrocinnamic acid content of 3.0%. Then, the resulting oily phase was charged in a 500 ml separatory funnel together with 165 g of a 1.8% sodium hydrogencarbonate aqueous solution. The amount of sodium hydrogencarbonate used in each of the first and second washing was 0.46 equivalent, respectively, i.e., 0.92 equivalent in total, per equivalent of dihydrocinnamic acid. The mixture was stirred at 400 rpm at room temperature for 20 minutes, followed by allowing to stand at room temperature for 1 hour to obtain 151 g of a washed oily phase. As a result of gas chromatography, the dihydrocinnamic acid content in the washed oily phase was found to be 0.60%, which corresponded to not more than 1% based on 3,4-dihydrocoumarin. The yield of 3,4-dihydrocoumarin in the above alkali washing was 96.8%.

While the invention has been described in detail and with reference to specific examples thereof, it will be apparent to one skilled in the art that various changes and modifications can be made therein without departing from the spirit and scope thereof.

What is claimed is:

1. A process for producing 3,4 -dihydrocoumarin comprising cyclization and dehydrogenation of a 3-(2-cyclohexanoyl)propionic acid ester, subjecting a reaction mixture obtained by said cyclization and dehydrogenation to distillation to remove high-boiling substances, and then subjecting a mixture obtained by distillation to rectification to recover 3,4-dihydrocoumarin.

2. A process for producing 3,4-dihydrocoumarin comprising cyclization and dehydrogenation of a 3-(2-cyclohexanoyl)propionic acid ester, washing a reaction mixture obtained by said cyclization and dehydrogenation with an alkali to reduce the dihydrocinnamic acid content of said reaction mixture to 1% by weight or less, wherein said washing with an alkali is carried out by using an alkali other than an alkali metal or alkaline earth metal hydroxide or by using not more than 1.5 equivalents of an alkali metal or alkaline earth metal hydroxide per equivalent of dihydrocinnamic acid, and then subjecting a mixture obtained by washing to rectification to recover 3,4-dihydrocoumarin.

3. A process for producing 3,4-dihydrocoumarin comprising cyclization and dehydrogenation of a 3-(2-cyclohexanyl)propionic acid ester, washing a reaction mixture obtained by said cyclization and dehydrogenation with an alkali to reduce the dihydrocinnamic acid content of said reaction mixture to 1% by weight or less, wherein said washing with an alkali is carried out by using an alkali other than an alkali metal or alkaline earth metal hydroxide or by using not more than 1.5 equivalents of an alkali metal or alkaline earth metal hydroxide per equivalent of dihydrocinnamic acid, and subjecting a mixture obtained by washing to distillation to remove high-boiling substances, and then subjecting a mixture obtained by distillation to rectification to recover 3,4 -dihydrocoumarin.

4. A process for producing 3,4-dihydrocoumarin comprising cyclization and dehydrogenation of a 3-(2-cyclohexanoyl)propionic acid ester, subjecting a reaction mixture obtained by said cyclization and dehydrogenation to distillation to remove high-boiling substances, and washing a mixture obtained by distillation with an alkali to reduce the dihydrocinnamic acid content of said reaction mixture to 1 % by weight or less, wherein said washing with an alkali is carried out by using an alkali other than an alkali metal or alkaline earth hydroxide or by using not more than 1.5 equivalents of an alkali metal or alkaline earth metal hydroxide per equivalent of dihydrocinnamic acid, and then subjecting a mixture obtained by washing to rectification to recover 3,4-dihydrocoumarin.

5. A process as claimed in claim 1, wherein said distillation is carried out so as to reduce the total content of o-ethylphenyl-3-cyclohexylpropionic acid and o-ethylphenyl dihydrocinnamate of said high-boiling substances to 2% by weight or less based on the amount of 3,4-dihydrocoumarin.

6. A process as claimed in claim 3, wherein said distilling is carried out so as to reduce the total content of o-ethylphenyl-3-cyclohexylpropionic acid and o-ethylphenyl dihydrocinnamate of said high-boiling substances to 2% by weight or less based on the amount of 3,4 -dihydrocoumarin.

7. A process as claimed in claim 4, wherein said distilling is carried out so as to reduce the total content of o-ethylphenyl-3-cyclohexylpropionic acid and o-ethylphenyl dihydrocinnamate of said high-boiling substances to 2% by weight or less based on the amount of 3,4-dihydrocoumarin.

* * * * *